US007922726B2

(12) United States Patent
White

(10) Patent No.: US 7,922,726 B2
(45) Date of Patent: Apr. 12, 2011

(54) SURGICAL TOOL HANDLE AND DISPOSABLE BROACH ASSEMBLY

(75) Inventor: Patrick White, West Chester, PA (US)

(73) Assignee: Greatbatch Medical S.A., Orvin (CH)

( * ) Notice: Subject to any disclaimer, the term of this patent is extended or adjusted under 35 U.S.C. 154(b) by 962 days.

(21) Appl. No.: 11/764,878

(22) Filed: Jun. 19, 2007

(65) Prior Publication Data

US 2008/0004628 A1 Jan. 3, 2008

Related U.S. Application Data

(60) Provisional application No. 60/806,360, filed on Jun. 30, 2006.

(51) Int. Cl.
*A61B 17/32* (2006.01)

(52) U.S. Cl. .......................... 606/86 R; 606/85; 81/492

(58) Field of Classification Search .................... 30/260; 81/489, 492; 407/29.1, 29.11–29.15; 409/264, 409/287; 606/79–85, 86 R, 99, 167–177
See application file for complete search history.

(56) References Cited

U.S. PATENT DOCUMENTS

D272,648 S 2/1984 Bolesky et al.
D273,806 S 5/1984 Bolesky et al.
4,765,328 A * 8/1988 Keller et al. .................... 606/85
4,921,493 A 5/1990 Webb, Jr. et al.
5,089,003 A * 2/1992 Fallin et al. ..................... 606/85
5,124,106 A 6/1992 Morr et al.
5,234,432 A * 8/1993 Brown ............................ 606/79
5,261,915 A * 11/1993 Durlacher et al. ............. 606/85
5,324,293 A 6/1994 Rehmann
5,342,362 A * 8/1994 Kenyon et al. .................. 606/79
5,454,815 A * 10/1995 Geisser et al. .................. 606/85
5,665,091 A 9/1997 Noble et al.
5,707,374 A * 1/1998 Schmidt .......................... 606/85
5,993,455 A 11/1999 Noble
6,120,508 A 9/2000 Grünig et al.

FOREIGN PATENT DOCUMENTS

WO WO 2006/061708 6/2006

* cited by examiner

*Primary Examiner* — Thomas C Barrett
*Assistant Examiner* — Larry E Waggle, Jr.
(74) *Attorney, Agent, or Firm* — Michael F. Scalise

(57) ABSTRACT

A surgical tool handle and separate disposable orthopedic tool head assembly is disclosed. The surgical tool handle has a reinforcing member extending from it. The reinforcing member is receivable in an internal bore of the disposable orthopedic tool head and provides structural reinforcement for the tool head. This reinforcement allows the use of disposable materials in the construction of the tool head that otherwise could not be use (e.g., plastic and resin materials) because of an increased risk of breakage or failure relative to metallic tool heads.

22 Claims, 6 Drawing Sheets

42
64
40
24
80
44
82A
28
16
20

42
64
40
24
44A
80A
28
16
20

91
60
64
66
70

SURGICAL TOOL HANDLE AND DISPOSABLE BROACH ASSEMBLY

The present application claims the benefit of prior filed U.S. Provisional Application Ser. No. 60/806,360 filed 30 Jun. 2006, to which the present application is a regular US national application, and which is fully incorporated herein by reference.

FIELD OF THE INVENTION

The present invention is in the field of orthopedic surgical instrumentation for particular use in a surgical procedure on bone structure, and relates to cutting devices particularly adapted to cut into bone or associated softer bone like tissues of the body, wherein a portion of a bone or associated cartilage is removed by a sharpened blade, chisel or a device having tooth-like projections which wear the bone or cartilage dawn by friction. More specifically, the present invention relates to disposable cutters and abraders on a handle, which are moved in a push-pull fashion, and have cutting formed prominences used to modify the shape of a bone or cartilage surface.

BACKGROUND OF THE INVENTION

Abraders, broaches, rasps and similar orthopedic surgical instruments are used in surgical procedures to modify bone structure. These instruments are adapted to cut into bone or associated softer bone-like tissues of the body to remove a portion of a bone or cartilage. Such instruments accomplish their purpose by means of tooth-like projections which wear or grind away the bone or cartilage. Typically, the tool head of these instruments is attached to a handle and perform its cutting function in a push-pull fashion.

The tool head of these instruments have cutting means formed on the cutting surface of the tool head in the form of prominences projecting from the tool head surface. The prominences or teeth act to modify the shape of a bone or cartilage when drawn across the surface to be modified.

Usually, these instruments are made of surgical steel or other metal alloys, and are designed for reuse. Reuse requires that the instrument be thoroughly cleaned and sterilized subsequent to its use, before it can be used again. It is the nature of the cutting surface on the tool head of these instruments to be covered with prominences that readily trap tissue debris during use. This tissue residue can be very difficult to remove from a tool head, especially from one with a particularly tortuous cutting surface. Even an intensive cleaning effort may not result in complete removal of all tissue residue.

Additionally, the subsequent sterilization of these tool heads does not tend to result in the removal of such debris from the cutting surface. The presence of tissue debris residue (even though sterilized) is a potential source of infectious material such as prions. A prion is a type of infectious agent made only of protein. Devices that are not properly cleaned and sterilized increase the risk of disease transfer from patient to patient. This is especially true following the emergence of certain prions that are not killed by normal hospital sterilization. Therefore, it would be beneficial to the field to have these tool heads available as disposable, one-time use items.

The field has been motivated to seek such a solution. For example, Geisser et al. (U.S. Pat. No. 5,454,815) disclose a one-time use bone rasp made of plastic. The working part of the Geisser rasp is made of a plastic material, and preferably, is provided with a hollow through bore from its proximal to its distal end. The through bore can be connected to a flush and suction line, to facilitate removal of cutting debris from the work site. However, because the tool head is made completely of plastic, and has an interior hollow through bore, there is the possibility of the tool head breaking during use. As another example, Grünig et al. (U.S. Pat. No. 6,120,508) disclose a one-time use surgical rasp having a two-piece tool head made of thin sheet metal sleeve, in the surface of which rasp teeth are formed. A plastic support is received in the sleeve, and the combination of the sleeve and plastic support are attached to a handle. Although the Grünig device may be useful for its intended purpose, it is still relatively complex, in that the tool head is a two-piece construction requiring the two mating steps: the support to the sleeve, and the combination to a handle.

Therefore, it would be beneficial to the field also to have a relatively simple, one-time use orthopedic cutting tool head made of plastic, but that has a reduced possibility of breaking during use.

SUMMARY OF THE INVENTION

The present invention is a reinforcing surgical tool handle combinable with disposable plastic surgical cutting tool head to provide a surgical tool handle and reinforced plastic surgical cutting tool assembly. The surgical tool holder/handle is specialized in that it is adapted to removably receive and securely hold a disposable surgical tool head, and to reinforce it during use. The plastic surgical broach used as an example in the embodiments illustrated below is merely an example of a type of disposable tool head. Other types of tool heads are anticipated and intended in the present invention, such as abraders, chisels, rasps and the like. In the embodiments illustrated, the tool head is made of a plastic material. Such materials can be soft and/or brittle relative to their metal counterparts in the field, and at risk of bending or breaking during use. Therefore, it is an object of the present holder/handle to include a means for internally reinforcing the disposable surgical tool head to reduce or prevent the risk of the tool head bending or braking during use. Referring now to the drawings, the details of preferred embodiments of the present invention are graphically and schematically illustrated.

The present surgical tool holder and disposable tool head combination assembly comprises, in main, a handle with a reinforcement member, a tool head, and a releasable locking mechanism to hold the head and the handle together for use. The reinforcing member extends from the tool interface on the surgical tool handle along an axis in the direction of the distal end of the tool head. The surgical tool head has an internal bore disposed to closely receive the reinforcing member. The handle interface on the tool head engages the tool interface on the handle when the reinforcing member is fully received in the internal bore. The handle interface on the tool head has a handle end catch means. The handle end catch means is disposed to selectably engage a pawl of a locking mechanism disposed in the handle proximate the tool interface of the handle.

The locking mechanism has a locking pawl, which is operable by the locking mechanism to releasably engage the catch means of the tool head when the reinforcing member is fully received in the internal bore. Engagement of the locking pawl with the catch means secures the position of the surgical tool head relative to the handle while the pawl is engaged with the catch means. In this configuration, the present invention combination surgical tool handle and disposable plastic tool head assembly is ready for use.

The combination of the reinforcement member in the present invention allows the use of disposable materials in the construction of the tool head that otherwise could not be use (e.g., plastic and resin materials) because of an increased risk of breakage or failure relative to metallic tool heads.

DETAILED DESCRIPTION OF THE INVENTION

Figure 1A:
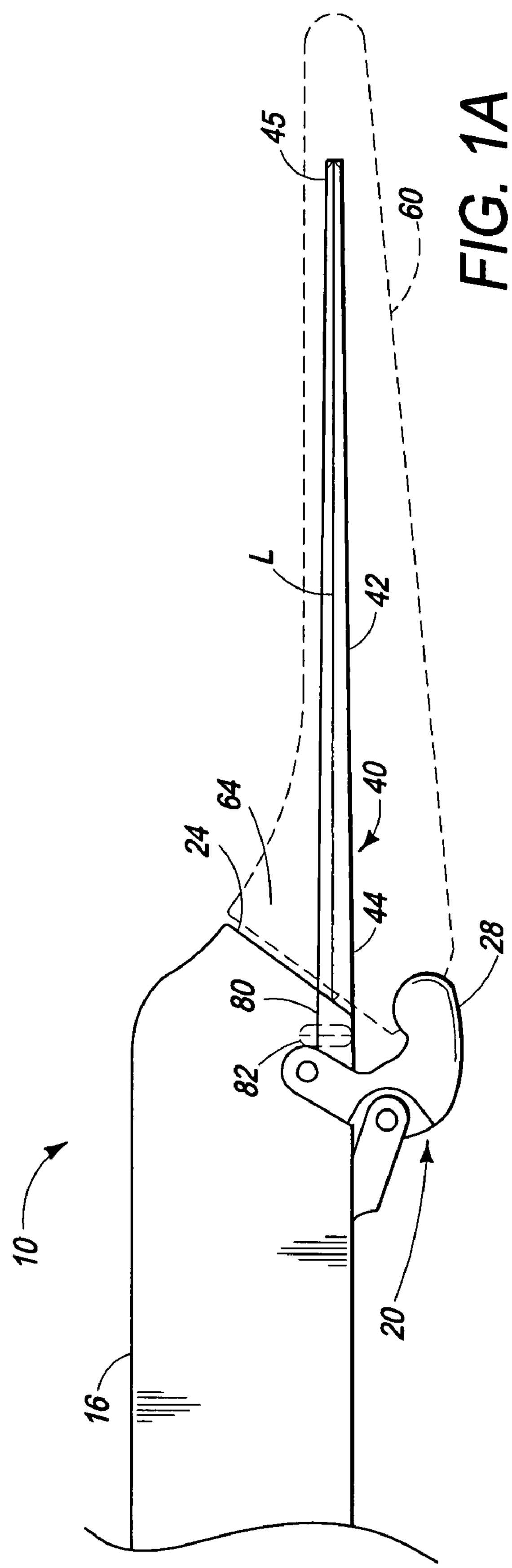
FIG. 1A is a side plan view of a combination surgical tool handle and disposable broach assembly of the present invention showing a portion of the handle with a reinforcing member extending from it.

Referring now to the drawings, the details of preferred embodiments of the present invention are graphically and schematically illustrated. Like elements in the drawings are represented by like numbers, and any similar elements are represented by like numbers with a different lower case letter suffix.

Figure 1B:
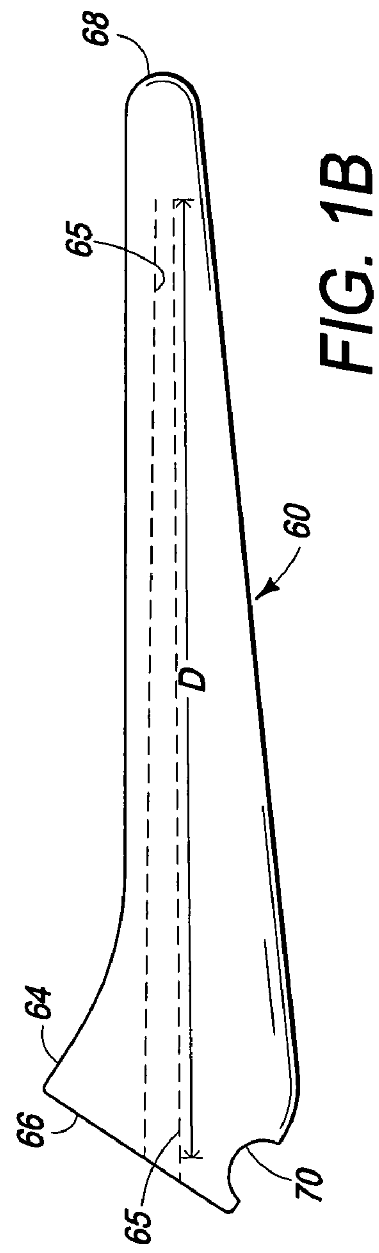
FIG. 1B is a side plan view of a disposable surgical tool head configured as a broach with an internal bore for closely receiving a reinforcing member.

As illustrated in FIGS. 1A and 1B, the present surgical tool holder 10 includes a handle 16 having a reinforcing member 40 for internally reinforcing a disposable surgical tool head 60 attached to the holder 10. The handle 16 in the preferred embodiments illustrated is know in the art as a surgical broach holder. Similar handles are described in detail in patent applications: U.S. Ser. No. 60/710,845 filed 24 Aug. 2004; U.S. Ser. No. 60/634,467, filed 9 Sep. 2004; and WO S/N PCT/IB2005/003720, filed 7 Dec. 2005, the contents of which are incorporated herein by reference. Other examples of handles similar to that of the present invention are described in U.S. Pat. No. 5,324,293 to Rehmann, and also in U.S. Pat. Nos. 5,665,091 and 5,993,455 to Noble. Other examples of handles suitable for practice in the present invention are known to and selectable by one of ordinary skill in the art in view of the figures and disclosure herein. The handle includes a locking mechanism 20 which engages a tool head 60 to securely attach the tool head 60 to the tool interface 24 of the handle 16.

Figures 1C, 1D:
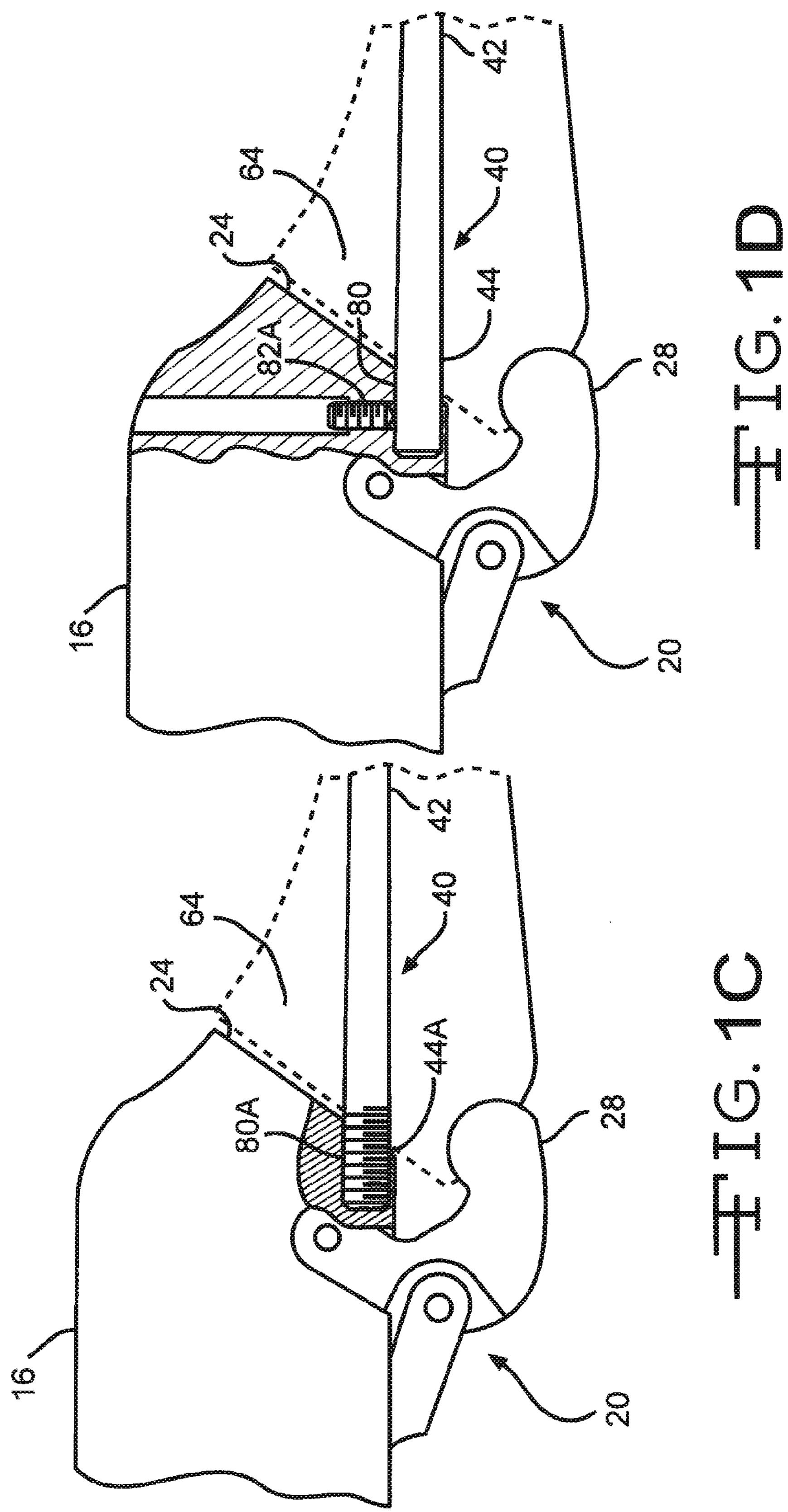
FIG. 1C is a side plan view of a threaded interface end 44A of a reinforcing rod 42 screwed into a complimentary threaded receiver 80A in the handle.
FIG. 1D is a side plan view of a set screw 82A screwed against a reinforcing rod 42 to secure it to the handle 16.
Figure 3A:
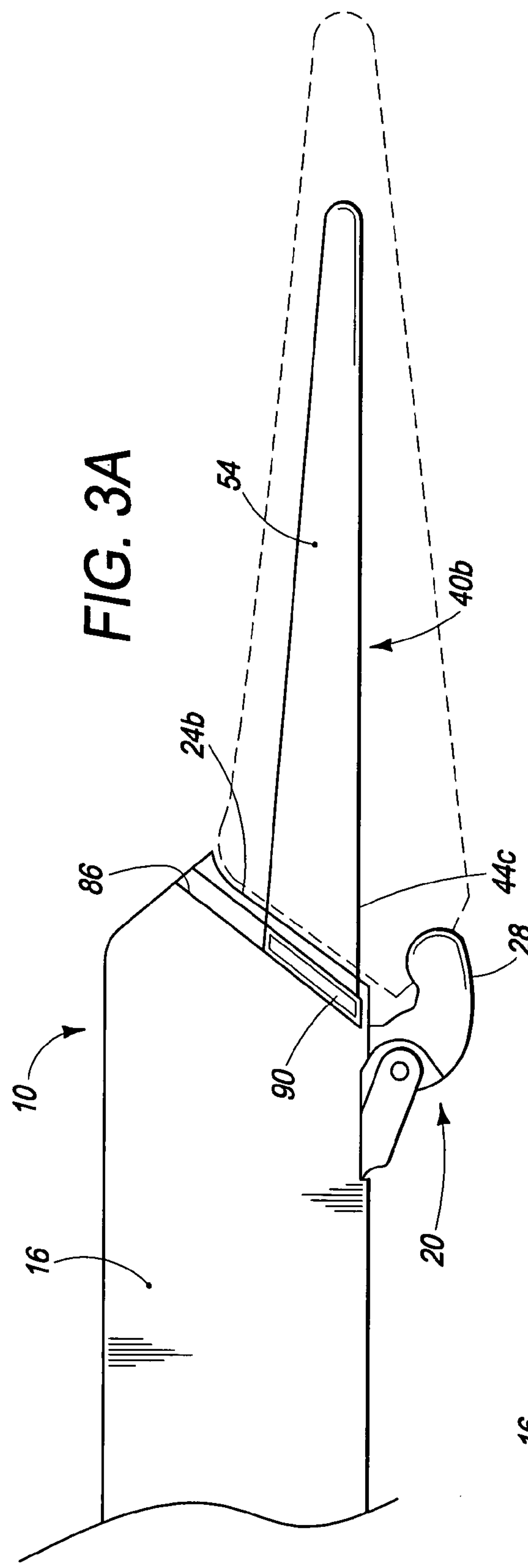
FIGS. 3A-3C are side plan views of an alternative embodiment of the assembly of the present invention illustrating an alternative configuration of the reinforcing member and the tool head bore, and an alternative configuration of the handle and tool head interfaces.

A reinforcing member 40 extends from the tool interface 24 on the handle 16, along a force axis 26 in the direction of the work. The reinforcing member 40 is made of a material that is compatible with the typical use and treatment of surgical tool handles in this field, and can take various configurations. Preferably, the reinforcing member is metal or a metallic alloy. Attachment of the reinforcing member 40 to the handle 16 can be in a variety of ways known to and selectable by one of ordinary skill in the art for practice in the present invention as exemplified below. In FIG. 1A, the reinforcing member 40 is a rod 42. In this preferred embodiment, the rod 42 is tapered at least slightly for its interface end 44 toward its distal end 45. The reinforcing rod 42 can be fixed into the handle 16 in any of a number of manners known to and selectable by the ordinary skilled artisan for practice in the present invention. For example, as illustrated in FIG. 1A, the rod 42 is accepted into a receiver 80 set into the tool interface 24 of the handle 16. In the figure, the rod 42 is retained in the receiver 80 by a retention pin 82 which passes through the rod 42 as shown. Alternatively, the interface end 44 of the rod 42 may be threaded 44A and screwed into a complimentary threaded receiver 80A (FIG. 1C), or rather than a retention pin 82 through the rod 42, a set screw 82A (FIG. 1D) in place of the retention pin 82 could be screwed against the rod 42 to secure it to the handle 16. A further alternative fixing mechanism is illustrated in FIG. 3A, as described below.

FIG. 1B shows a tool head 60 for practice in the present assembly 10. In this preferred embodiment the tool head 60 is configured as a surgical broach. The tool head 60 has a tool bore 65 partially extending from the handle interface 66 at the interface end 64 of the tool 60 toward the distal/work end 68 of the tool head 60. The tool bore 65 is configured to very closely receive the rod 42 and to engage the rod 42 with a friction force when the rod 42 is pressed into the rod bore 65.

The tool head 60 also has a catch means 70 disposed to be engaged by the locking mechanism 20 of the handle 16. In the example illustrated, the catch means 70 is a notch engageable by the pawl 28 of the locking mechanism 20. Engagement of the locking mechanism 20 with the tool catch 70 acts to prevent the tool head 60 from sliding on the reinforcing rod 42, and to prevent (in combination with the angle of the interfaces 24 and 66 between the handle 16 and the tool head 60) rotation of the tool head 60 about the rod 42.

Figures 2A, 2B, 2C:
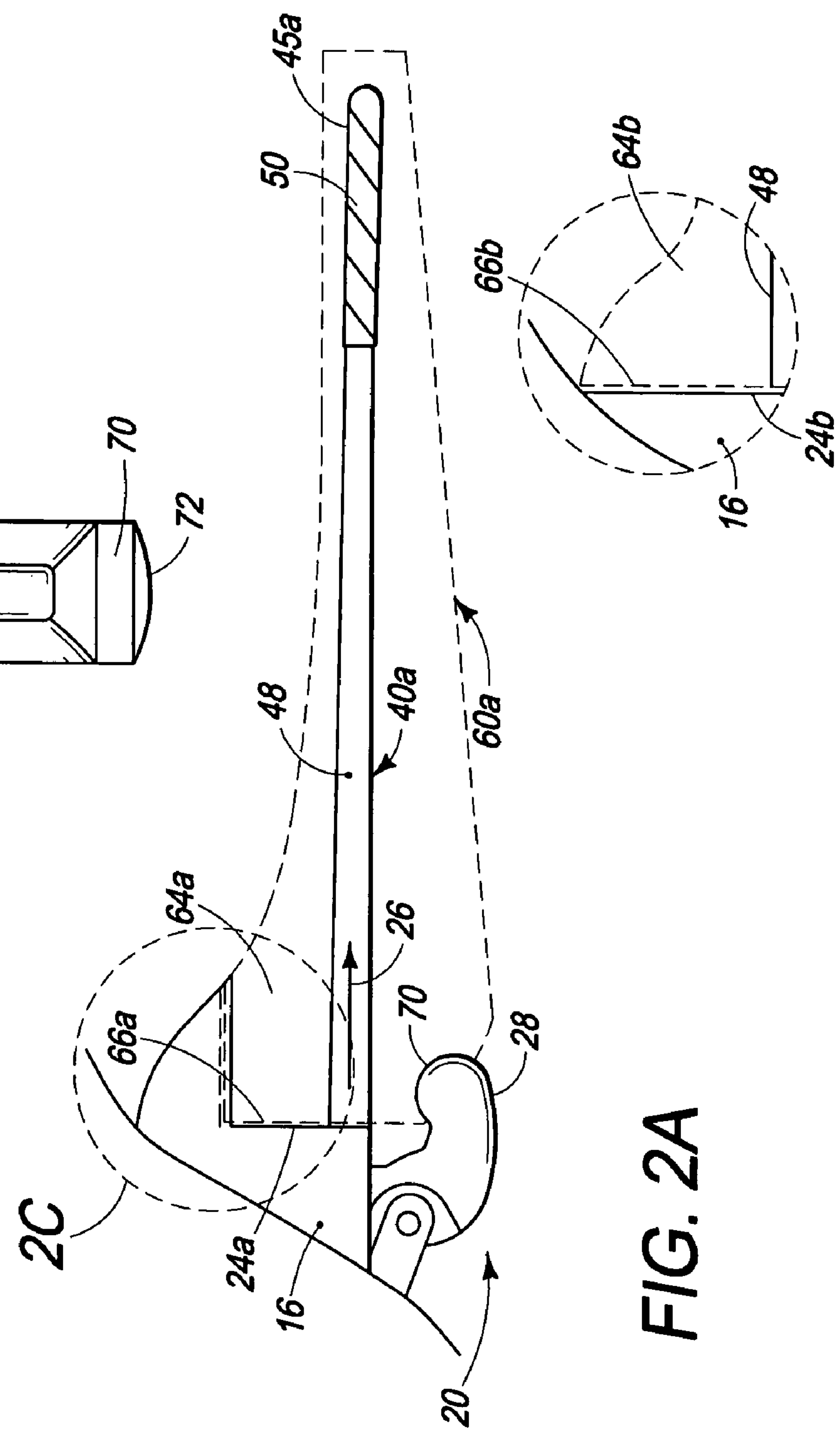
FIG. 2A is a side plan view of the assembly of the present invention showing a portion of the handle with a partially threaded reinforcing member extending from it.
FIG. 2B is a side plan view of a disposable surgical tool head configured to be threaded onto the reinforcing member.
FIG. 2C is a view of the insert of FIG. 2A showing an alternative configuration of the handle and tool head interfaces.
Figure 4A:
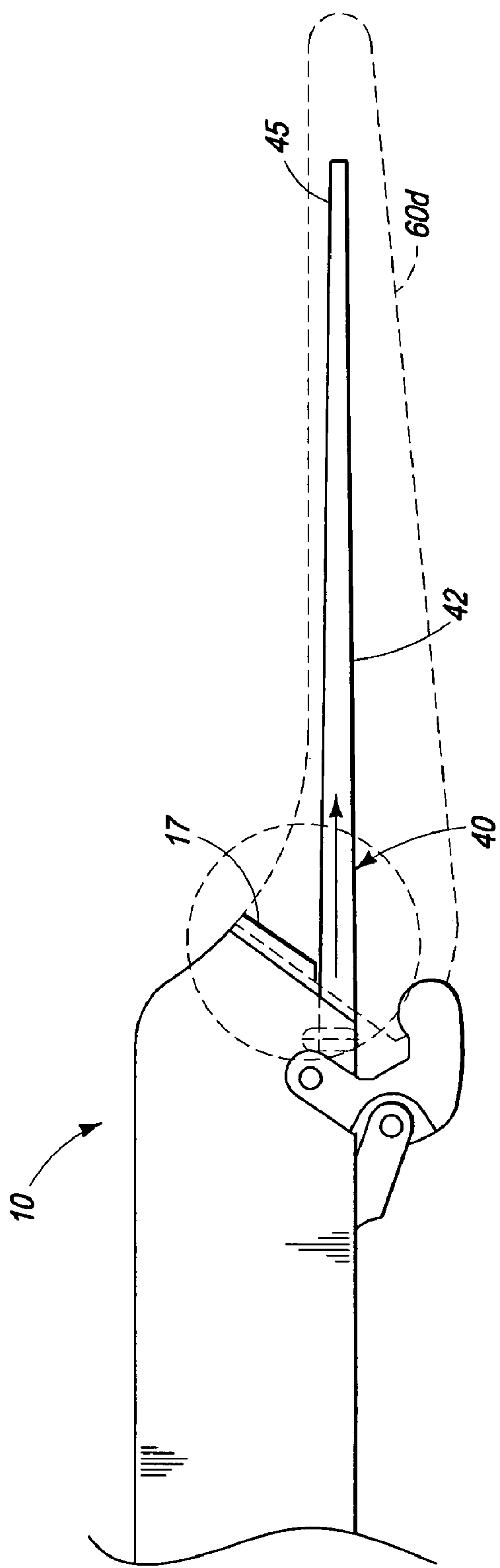
FIGS. 4A and 4B are (A) a side plan view of an assembly of the present invention showing a portion of the handle with a locking tongue extending from the tool interface, and (B) a rear plan view of the corresponding locking groove on the handle interface of the tool head.
Figure 4B:
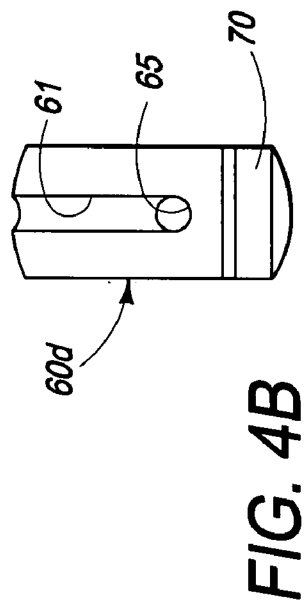

As illustrated in FIGS. 2A and 2B, in another preferred embodiment the reinforcing member 40 is a partially threaded rod 48 having a thread 50 disposed at the distal end 45*a* of the threaded rod 48. The threaded portion can be practiced at another portion along the length L of the reinforcing member 40 as selectable by the ordinary skilled artisan. In this embodiment, the handle 16 has a flat tool interface 24*a* and the tool head 60 has a flat handle interface 66*a* at its interface end 64*b*, i.e., the interfaces 24*a* and 66*a* are perpendicular to the force axis 26 of the reinforcing member 40*a*. The thread 50 can be a self-tapping, but preferably screws into a complementary pre-tapped bottom-portion 69 of the bore 65. Alternatively, the tool head 60*a* can have a threaded fastener (not shown) set into the bottom portion 69 of the bore 65, into which the thread 50 of the threaded reinforcing rod 48 can be screwed. Referring now to FIGS. 4A and 4B, unwanted rotation of the tool head 60*d* may further be prevented by a locking tongue 17 extending from the tool interface 24 of the handle 16. The locking tongue 17 which enters a corresponding groove 61 at the interface end 64*b* of the handle interface 66 of the tool head 60*d*, and when engaged therewith rotation of the tool head 60*d* is further prevented.

In this embodiment, as further illustrated in FIG. 2B, the interface end 64*a* of the tool head 60*a* is configured with arcuate portions 72 to rotate without obstruction relative to the handle 16. FIG. 2C illustrates an example of an alternative configuration of the relationship of the handle and tool interfaces 24*b* and 66*b* relative to each other to allow their rotation without obstruction relative to the each other. As in the examples above, this embodiment utilizes a lock catch notch 70 to be engaged by the pawl 28 of the locking mechanism 20. Engagement of the locking mechanism 20 with the tool catch 70 acts to prevent the tool head 60 from rotating about the rod 42.

Figure 3B:
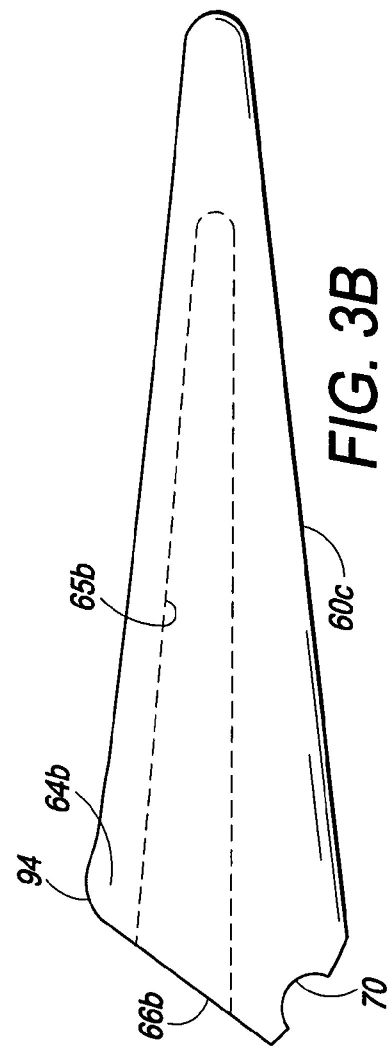
Figure 3C:
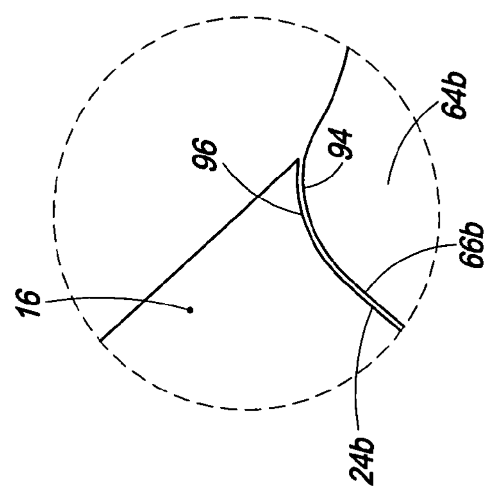

FIGS. 3A-3C illustrate an alternative preferred embodiment of the assembly 10 of the present invention having an alternative configuration of the reinforcing member 40, the tool head bore 65*b*, and the handle and tool head interfaces 24*b* and 66*b*. Additionally shown in the figures is a further alternative mechanism for fixing the reinforcing rod 40*b* to the tool interface 24*b* of the handle 16. In this embodiment, the reinforcing member 40*b* is a blade 54 having a somewhat flat configuration, and has an interface end 44*c* terminating in a T-fitting 90. A blind-ended channel 86 is disposed proximate the tool interface 24*b* and communicates at its open end with the surface of the handle 16. As illustrated, the T-fitting 90 at the interface end 44*c* of the reinforcing member 40*b* is slid into the channel 86. The bore 65*b* of the tool head 60*c* is slid over the reinforcing blade 54. A shoulder 94 is provided on the handle interface 66*b*. The tool head 60*c* is received against a seat 96 on the tool interface 24*b* of the handle 16. Once the shoulder 94 and the seat 96 are engaged, the locking mechanism 20 is set and the tool head 60*c* is prevented from sliding or twisting relative to the handle 16. Additionally, the disposition of the shoulder 94 against the seat 96 prevents the T-fitting 90 of reinforcing blade 54 from sliding out of the channel 86.

Figure 5:
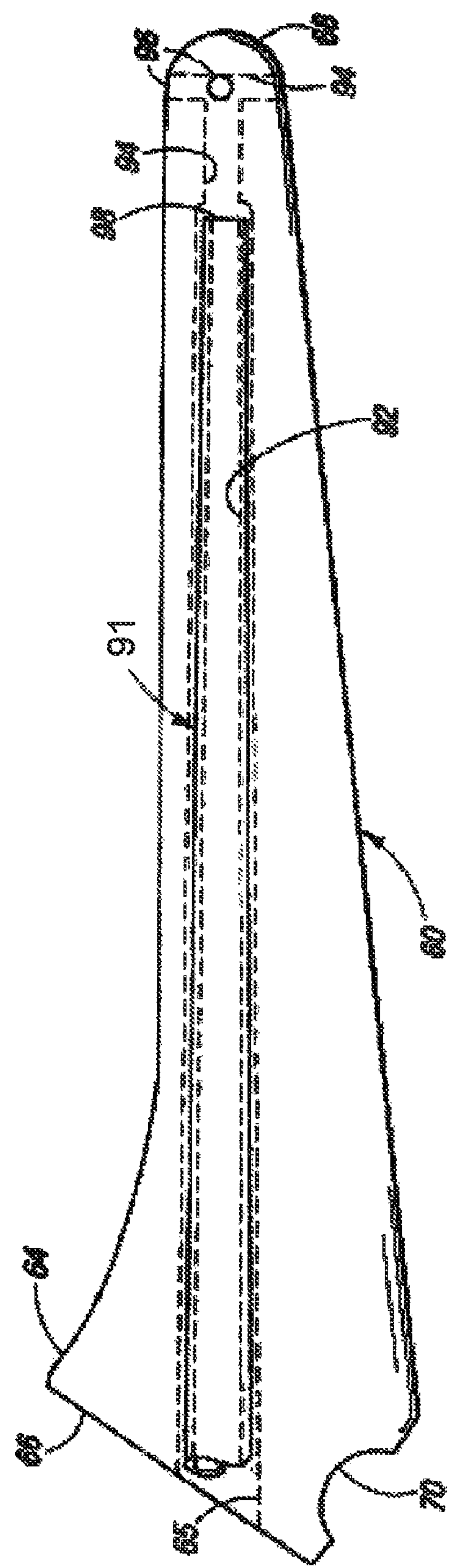
FIG. 5 is a schematic side view of a reinforcing member received within the bore of a tool head, the reinforcing member incorporating a hollow tube connecting with a fluid chamber and outlets on the working surface of the tool head, to provide a lavage capability when using the present invention.

In an alternative preferred embodiment illustrated in FIG. 5, the reinforcing member 91 of the surgical tool handle has an inner flow passage 92 along at least a portion of the length L of the reinforcing member. In the embodiment illustrated, the flow passage is through the entire length of the reinforcing member 91. At the handle 16, the flow passage 92 communicates with a proximal in/out port (not shown), which is connectable to a suction or liquid source. One or more delivery ports 98 are disposed along the length L of the hollow reinforcing member 91. The delivery ports communicate with a flow chamber system 94 disposed within the tool head 60. The flow chamber system 94 further communicates with one or more outer surface ports 96 in the outer surface of the tool head 60. In this embodiment, a lavage liquid can be delivered to or removed from the work site.

While the above description contains many specifics, these should not be construed as limitations on the scope of the invention, but rather as exemplifications of one or another preferred embodiment thereof. Many other variations are possible, which would be obvious to one skilled in the art. Accordingly, the scope of the invention should be determined by the scope of the appended claims and their equivalents, and not just by the embodiments.

What is claimed is:

1. A surgical tool handle, which comprises:

a) a surgical tool handle;

b) a reinforcing member comprising a first length extending from a distal reinforcing member portion having a distal end to a spaced apart proximal reinforcing member portion connectable to the tool handle; and c) a locking mechanism comprising a locking pawl having a second length extending from a distal locking pawl portion to a proximal locking pawl portion pivotably attached to the tool handle, wherein the locking pawl is pivotable between a locked position with the distal locking pawl portion seatable in a catch of a surgical tool head secured to the tool handle with the reinforcing member received in an internal bore of the tool head, and an unlocked position with the distal locking pawl portion free of the tool head catch; and d) wherein in the locked position, the distal locking pawl portion seatable in a catch of a surgical tool head is spaced from the tool handle by a first distance that is less than a second distance measured from the distal end of the reinforcing member to the tool handle.

2. The surgical tool handle of claim 1 wherein the reinforcing member has a blade-shaped configuration.

3. The surgical tool handle of claim 1 wherein the reinforcing member has a rod-shaped configuration.

4. The surgical tool handle of claim 3 wherein the reinforcing member has a tapered rod-shaped configuration.

5. The surgical tool handle of claim 1 wherein the reinforcing member has an outer surface along at least a portion of which a bore engagement feature is disposed, the bore engagement feature being adapted to engage a surface of an internal bore of a surgical tool head when the reinforcing member is fully received in the internal bore.

6. The surgical tool handle of claim 5 wherein the bore engagement feature of the reinforcing member is a friction engagement surface.

7. The surgical tool handle of claim 5 wherein the reinforcing member is a rod and the bore engagement feature is a threaded outer surface of the rod.

8. The surgical tool handle of claim 1 wherein the reinforcing member has an inner flow passage along at least a portion of its first length, the inner flow passage communicating with a port proximate the tool handle.

9. The surgical tool handle of claim 1 wherein the reinforcing member is connectable to a receiver set into the tool interface of the tool handle and retainable there by a retention mechanism selected from the group consisting of a retention pin which passes through the rod, a complementary threaded interface between the reinforcing member and the receiver, and a set-screw screwed against the reinforcing member to secure the member in the receiver.

10. The surgical tool handle of claim 1 wherein the reinforcing member is made of a metal.

11. The surgical tool handle of claim 1 wherein the tool interface of the handle has a perpendicular locking tongue extending from it, the locking tongue being closely receivable in a corresponding tongue groove at a handle interface of a tool head, and when received therein rotation of the tool head is prevented.

12. The surgical tool handle of claim 1 wherein the first length of the reinforcing member is significantly longer than the second length of the locking pawl.

13. The surgical tool handle of claim 1 wherein in the locked position, the first distance is significantly shorter than the second distance.

14. The surgical tool handle of claim 1 wherein the tool handle has a flat tool interface against which an interface of a tool head seats when the reinforcing member is received in an interior bore of the tool head.

15. A surgical tool handle, which comprises:

a) a surgical tool handle;

b) a reinforcing member comprising a first length extending from a distal reinforcing member portion having a distal end to a spaced apart proximal reinforcing member end integral with the tool handle;

c) a locking mechanism comprising a locking pawl having a second length extending from a distal locking pawl portion to a proximal locking pawl portion pivotably connected to the tool handle, wherein the locking pawl is pivotable between a locked position with the distal locking pawl portion seatable in a catch of a surgical tool head secured to the tool handle with the reinforcing member received in an internal bore of the tool head, and an unlocked position with the distal locking pawl portion free of the tool head catch; and d) wherein in the locked position, the distal locking pawl portion seatable in a catch of a surgical tool head is spaced from the tool handle by a first distance that is less than a second distance measured from the distal end of the reinforcing member to the tool handle.

16. The surgical tool handle of claim 15 wherein the first length of the reinforcing member is significantly longer than the second length of the locking pawl.

17. The surgical tool handle of claim 15 wherein in the locked position, the first distance is significantly shorter than the second distance.

18. A surgical tool handle, which comprises:

a) a surgical tool handle;

b) a reinforcing member comprising a first length extending from a distal reinforcing member portion having a distal end to a spaced apart proximal reinforcing member end connected to the tool handle;

c) a locking mechanism comprising a locking pawl having a second length extending from a distal locking pawl distal portion to a proximal locking pawl portion connected to the tool handle, wherein the locking pawl is movable between a locked position with the distal locking pawl portion seatable in a catch of a surgical tool head secured to the tool handle with the reinforcing member received in an internal bore of the tool head, and an unlocked position with the distal locking pawl portion free of the tool head catch; and d) wherein in the locked position, the distal locking pawl portion seatable in a catch of a surgical tool head is spaced from the tool handle by a first distance that is less than a second distance measured from the distal end of the reinforcing member to the tool handle.

19. The surgical tool handle of claim 18 wherein the first length of the reinforcing member is significantly longer than the second length of the locking pawl.

20. The surgical tool handle of claim 18 wherein in the locked position, the first distance is significantly shorter than the second distance.

21. The surgical tool handle of claim 18 wherein the reinforcing member is detachable from the tool handle.

22. A surgical tool handle, which comprises:

a) a surgical tool handle;

b) a reinforcing member comprising an outer surface having a first length extending from a distal reinforcing member portion including a distal end to a spaced apart proximal reinforcing member portion connected to the tool handle, wherein at least a portion of the outer surface is threaded;

c) a locking mechanism comprising a locking pawl having a distal locking pawl portion extending to a proximal locking pawl portion pivotably attached to the tool handle, wherein the locking pawl is pivotable between a locked position with the distal locking pawl portion seatable in a catch of a surgical tool head secured to the tool handle with the reinforcing member received in an internal bore of the tool head and an unlocked position with the distal locking pawl portion free of the tool head catch; and d) wherein the threaded outer surface of the reinforcing member is adapted to threadingly engage the internal bore of a surgical tool head when the reinforcing member is fully received in the internal bore.

* * * * *